(12) United States Patent
Mihalca et al.

(10) Patent No.: US 10,783,626 B2
(45) Date of Patent: Sep. 22, 2020

(54) VIDEO ENDOSCOPIC SYSTEM

(71) Applicant: Smith & Nephew, Inc., Memphis, TN (US)

(72) Inventors: Gheorghe Mihalca, North Chemlsford, MA (US); Baoduy Tran, Wilmington, MA (US); Carlos A. Rodriguez, Wakefield, MA (US)

(73) Assignee: SMITH & NEPHEW, INC., Memphis, TN (US)

( * ) Notice: Subject to any disclaimer, the term of this patent is extended or adjusted under 35 U.S.C. 154(b) by 43 days.

(21) Appl. No.: 15/474,752

(22) Filed: Mar. 30, 2017

(65) Prior Publication Data
US 2017/0202443 A1 Jul. 20, 2017

Related U.S. Application Data

(62) Division of application No. 14/380,474, filed as application No. PCT/US2013/027436 on Feb. 22, 2013, now Pat. No. 9,715,727.
(Continued)

(51) Int. Cl.
*H04N 1/60* (2006.01)
*G06T 7/00* (2017.01)
(Continued)

(52) U.S. Cl.
CPC ........ *G06T 7/0012* (2013.01); *A61B 1/00029* (2013.01); *A61B 1/00045* (2013.01); *A61B 1/00124* (2013.01); *A61B 1/00135* (2013.01); *A61B 1/04* (2013.01); *A61B 1/042* (2013.01); *A61B 1/0669* (2013.01); *A61B 1/0676* (2013.01); *A61B 1/0684* (2013.01); *A61B 1/317* (2013.01); *G02B 23/2469* (2013.01); *G02B 23/2484* (2013.01); *G06K 9/46* (2013.01); *G06K 9/4652* (2013.01); *G06T 7/11* (2017.01); *G06T 7/136* (2017.01); *G06T 7/90* (2017.01); *G06T 11/001* (2013.01); *H04N 1/6008* (2013.01); *H04N 5/2256* (2013.01);
(Continued)

(58) Field of Classification Search
CPC ............ H04N 5/23241; H04N 5/2256; H04N 2005/2255
See application file for complete search history.

(56) References Cited

U.S. PATENT DOCUMENTS

| 4,969,450 A | 11/1990 | Chinnock et al. |
| 6,092,722 A | 7/2000 | Heinrichs et al. |

(Continued)

FOREIGN PATENT DOCUMENTS

| CN | 1642467 | 7/2005 |
| CN | 1777391 | 5/2006 |

(Continued)

OTHER PUBLICATIONS

3rd Exam Report for AU App No. 2013222242 dated Jul. 10, 2018, 5 pages.
(Continued)

*Primary Examiner* — Antonio A Caschera

(57) ABSTRACT

Image data representing an image captured by a video endoscopic device is converted from a first color space to a second color space. The image data in the second color space is used to determine the location of features in the image.

11 Claims, 8 Drawing Sheets

Related U.S. Application Data

(60) Provisional application No. 61/708,157, filed on Oct. 1, 2012, provisional application No. 61/668,743, filed on Jul. 6, 2012, provisional application No. 61/602,106, filed on Feb. 23, 2012.

(51) Int. Cl.
| | |
|---|---|
| *G06T 7/11* | (2017.01) |
| *G06T 7/90* | (2017.01) |
| *G06T 7/136* | (2017.01) |
| *A61B 1/00* | (2006.01) |
| *A61B 1/04* | (2006.01) |
| *A61B 1/317* | (2006.01) |
| *G02B 23/24* | (2006.01) |
| *G06K 9/46* | (2006.01) |
| *A61B 1/06* | (2006.01) |
| *G06T 11/00* | (2006.01) |
| *H04N 5/225* | (2006.01) |

(52) U.S. Cl.
CPC .. *A61B 1/00103* (2013.01); *G06K 2009/4666* (2013.01); *G06T 2207/10016* (2013.01); *G06T 2207/10024* (2013.01); *G06T 2207/10068* (2013.01); *G06T 2207/30008* (2013.01); *H04N 2005/2255* (2013.01)

(56) References Cited

U.S. PATENT DOCUMENTS

| | | | |
|---|---|---|---|
| 6,099,465 A | 8/2000 | Inoue | |
| 6,895,279 B2 | 5/2005 | Loeb et al. | |
| 7,397,364 B2 | 7/2008 | Govari | |
| 7,582,056 B2 | 9/2009 | Noguchi et al. | |
| 7,668,450 B2 | 2/2010 | Todd et al. | |
| 7,914,443 B2 | 3/2011 | Uchimura et al. | |
| 8,029,439 B2 | 10/2011 | Todd et al. | |
| 8,246,230 B2 | 8/2012 | Todd et al. | |
| 8,290,600 B2 | 10/2012 | Hastings et al. | |
| 8,599,250 B2 | 12/2013 | Amling et al. | |
| 8,672,922 B2 | 3/2014 | Loh et al. | |
| 8,723,936 B2 | 5/2014 | Amling et al. | |
| 9,089,255 B2 | 7/2015 | Kato | |
| 2002/0138008 A1* | 9/2002 | Tsujita | A61B 1/00009 600/473 |
| 2004/0147809 A1 | 7/2004 | Kazakevich | |
| 2006/0116550 A1* | 6/2006 | Noguchi | A61B 1/015 600/132 |
| 2006/0171693 A1 | 8/2006 | Todd et al. | |
| 2008/0239070 A1* | 10/2008 | Westwick | A61B 1/0638 348/68 |
| 2010/0124365 A1 | 5/2010 | Kanda | |
| 2010/0179384 A1 | 7/2010 | Hoeg et al. | |
| 2010/0208047 A1 | 8/2010 | Kitamura | |
| 2011/0013242 A1 | 1/2011 | Hagio et al. | |
| 2011/0018988 A1* | 1/2011 | Kazakevich | A61B 1/00016 348/68 |
| 2011/0193948 A1 | 8/2011 | Amling et al. | |
| 2011/0301447 A1 | 12/2011 | Park et al. | |
| 2012/0088970 A1 | 4/2012 | Kato et al. | |
| 2013/0158350 A1 | 6/2013 | Juergens | |
| 2013/0338438 A1 | 12/2013 | Watanabe | |
| 2014/0184771 A1 | 7/2014 | Mazzetti et al. | |
| 2017/0354316 A1* | 12/2017 | Mihalca | A61B 1/00016 |

FOREIGN PATENT DOCUMENTS

| | | |
|---|---|---|
| CN | 101021946 | 8/2007 |
| CN | 101106936 | 1/2008 |
| CN | 101739659 | 6/2010 |
| CN | 102057681 | 5/2011 |
| EP | 1998165 A1 | 1/2007 |
| EP | 1998165 | 12/2008 |
| EP | 2085019 A1 | 8/2009 |
| EP | 2156782 A1 | 2/2010 |
| EP | 2609849 A1 | 12/2012 |
| JP | S63-256916 | 10/1988 |
| JP | H10-216144 A | 8/1998 |
| JP | H10-309258 A | 11/1998 |
| JP | 2001-145003 A | 5/2001 |
| JP | 2004-024656 | 1/2004 |
| JP | 2007-307397 | 11/2007 |
| JP | 2009302960 | 12/2009 |
| JP | 2010-115413 A | 5/2010 |
| WO | 03022135 A2 | 3/2003 |
| WO | 2006/037034 A2 | 4/2006 |
| WO | 2011005865 A2 | 1/2011 |
| WO | 2011005865 | 4/2011 |
| WO | 2013084975 A1 | 6/2013 |
| WO | 13100030 A1 | 7/2013 |
| WO | 2013/121616 A1 | 8/2013 |
| WO | 20131/21610 A1 | 8/2013 |
| WO | 2013/1146014 A1 | 10/2013 |
| WO | 2014195843 A2 | 12/2014 |
| WO | 2015000554 A1 | 1/2015 |

OTHER PUBLICATIONS

Examination Report in Australian Patent Application No. 12013222242; dated Apr. 18, 2018; 3 pages.
Office Action in Chinese Patent Application No. 201380021383.4; dated Feb. 24, 2018; 3 pages.
Office Action in Chinese Patent Application No. 201380021383.4 dated Jun. 8, 2017, 11 pages.
Wu Chia-Hsiang, et al., "Automatic extraction and visualization of human inner structures from endoscopic image sequences," Proceedings of SPIE, vol. 5369, Apr. 30, 2004 (Apr. 30, 2004), pp. 464-473.
R.C. Gonzalez, et al.,"Chapter 10 (Image Segmentation)", Jan. 1, 2002 (Jan. 1, 2002), Digital Image Processing, Prentice-Hall, Upper Saddle River, NJ, USA, pp. 567-642.
First Office Action in Chinese Patent Application No. 201380021383. 4, dated May 11, 2016.
Office Action in Russian Patent Application No. 2014136476/14(059047); dated Sep. 9, 2017; 5 pages.
Office Action in Japanese Patent Application No. 2014-558895; dated Dec. 21, 2018; 10 pages.
Office Action in European Patent Application No. 13708317.6-1210; dated Feb. 9, 2018; 6 pages.
Office Action in European Patent Application No. 15167727.5; dated Apr. 28, 2017; 4 pages.
Office Action dated Jul. 11, 2017 in Australian patent application No. 2013222242, 4 pages.
Second Office Action in Russian patent application No. 2014136476; dated Apr. 13, 2017; 5 pages.
Office Action for Japanese Patent Application No. 2014-558895 dated Feb. 6, 2017; 6 pages.
Office Action for Russian Patent Application No. 2014136476 dated Dec. 20, 2016; 6 pages.
Office Action in Japanese Patent Application No. 2018-031755; dated Jan. 11, 2019; 5 pages.
Office Action in Korean Patent Application No. 10-2014-7026046; dated Nov. 9, 2018; 4 pages.
Office Action in Japanese Patent Application No. 2014-558895; dated Oct. 30, 2017; 3 pages.
European examination report dated Apr. 24, 2019 in European patent application 15167727.5-1008; 4 pages.
Australian examination report dated Apr. 26, 2019 in Australian patent application 201805109; 4 pages.
Japanese Patent Office, Non-Final Office Action dated Jun. 17, 2019 in corresponding Japanese application 2014-558895; 4 pages.
European Application No. 15167727.5-1008 Examination Report dated Dec. 16, 2019.
Korean Intellectual Property Office, Notice of Final Rejection dated Jun. 21, 2019 in corresponding Korean application 10-2014-7026046; 5 pages.

(56) References Cited

OTHER PUBLICATIONS

Indian Application No. 7449/DELNP/2014 Examination Report dated Jan. 30, 2020.
JP Office Action for Application No. 2018-031755 dated Feb. 12, 2020, 2 pages.
AU Office Action for App No. 2018205109 dated Apr. 20 2020, 6 pages.
EP Office Acton for App No. 13708317,6 dated Mar. 3, 2020, 13 pages.
Brazilian Application No. BR112014020781-0—Informal Translation of the Preliminary Office Action dated Dec. 26, 2019.

\* cited by examiner

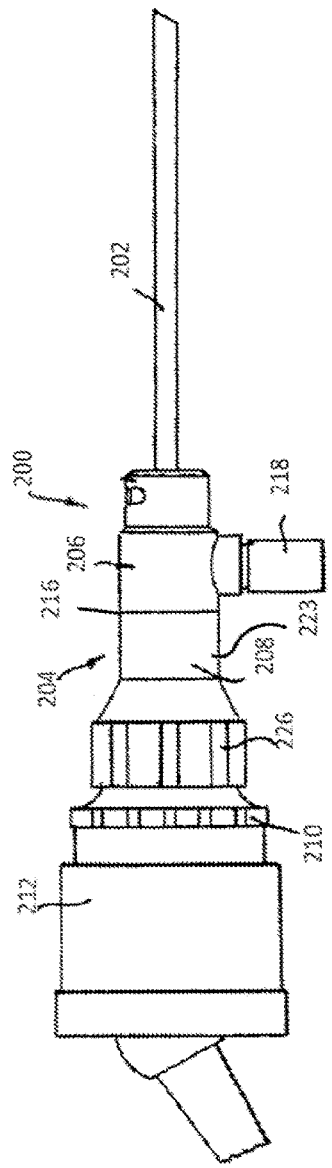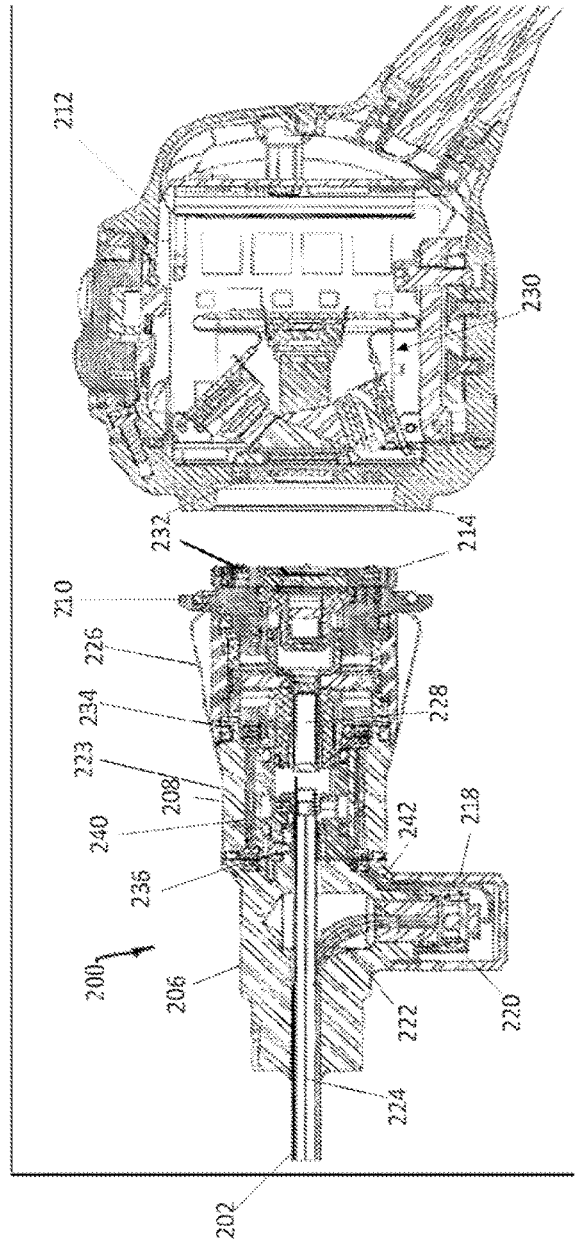

VIDEO ENDOSCOPIC SYSTEM

CROSS-REFERENCE TO RELATED APPLICATIONS

This application is a divisional of U.S. application Ser. No. 14/380,474 filed Aug. 22, 2014. The Ser. No. 14/380,474 is a U.S. National Stage Application, submitted under 35 U.S.C. 371, claiming priority to PCT International Application No. PCT/US2013/027436 filed Feb. 22, 2013 titled "VIDEO ENDOSCOPIC SYSTEM." The PCT/US2013/027436 claims priority to each of U.S. Provisional Application No. 61/708,157 filed Oct. 1, 2012 titled "ENDOSCOPE WITH LED ILLUMINATION," U.S. Provisional Application No. 61/668,743 filed Jul. 6, 2012 titled "ENDOSCOPE WITH LED ILLUMINATION," and U.S. Provisional Application No. 61/602,106 filed Feb. 23, 2012 titled "ENDOSCOPE WITH LED ILLUMINATION." All the prior applications are incorporated by reference herein as if reproduced in full below.

TECHNICAL FIELD

This document relates to video endoscopic systems.

BACKGROUND

Medical endoscopes are used to inspect regions within the body (e.g., cavities, joints) during surgery (such as laparoscopic/thoracoscopic surgery) through a small puncture. In some cases, the endoscope includes a rigid or flexible elongated insertion tube equipped with a set of optical fibers that extend from a proximal handle through the insertion tube to the distal viewing tip of the endoscope. A light source provides light to the optical fibers so that the region to be inspected is illuminated.

SUMMARY

In one aspect, an image data representing an image captured by a video endoscopic device is accessed. The image data is encoded in a first color space. The accessed image data is converted from the first color space to a second color space. The second color space is different than the first color space. A location of a feature in the image is identified by analyzing the image data in the second color space. Segmentation data that indicates the location of the features in the image is stored and, based on the segmentation data, the image is displayed with an indication of the identified location of the features.

Implementations may include one or more of the following features. Displaying the image with an indication of the identified location of the features comprises may include converting the image data from the second color space to a third color space and displaying, based on the segmentation data and the image data in the third color space, the image with an indication of the identified location of the features. The one or more features may include a type of tissue, an anatomical structure, or an external object introduced into a patient.

Identifying the location of the feature in the image by analyzing the image data in the second color space may include generating a histogram of hue values of pixels in the image data based on the image data in the second color space and identifying pixels that fall within a range of hues in the histogram that correspond to the features, wherein the segmentation data indicates the pixels falling with the range of hues in the histogram that correspond to the features.

Identifying the location of the feature in the image by analyzing the image data in the second color space may include grouping pixels in the image data in the second color space into groups based on hue values of the pixels; determining a first group of pixels from among the groups of pixels; determining a second group of pixels from among the groups of pixels; and selecting one of the first or second group of pixels based on a relative color difference between the first and second groups of pixels, wherein the segmentation data indicates the selected group of pixels. Grouping pixels may include generating a histogram of hue values of pixels in the image data based on the image data in the second color space. Determining a first group of pixels may include determining a first set of pixels that fall within a first range of the hues in the histogram. Determining a second group of pixels may include determining a second set of pixels that fall within a second range of hues in the histogram. Selecting one of the first or second group of pixels may include selecting one of the first or second set of pixels based on a relative color difference between the first range of hues and the second range of hues.

The first color spaces may be one of RGB, YUV, YPrPb, or YcrCb. The second color space may be one of HSV, Lab, or HSY.

In another aspect a system includes a video endoscopic device and a computing device. The video endoscopic device is configured to generate image data representing an image captured by the video endoscopic device, wherein the image data is encoded in a first color space and transmit the image data to a computing device. The computing device is configured to receive the image data transmitted by the video endoscopic device; convert the received image data from the first color space to a second color space, wherein the second color space is different than the first color space; identify a location of a feature in the image by analyzing the image data in the second color space; store segmentation data that indicates the location of the features in the image; and display, based on the segmentation data, the image on a display device with an indication of the identified location of the features.

Implementations may include one or more of the following features. For example, to display the image on the display device with an indication of the identified location of the features, the computing device may be configured to convert the image data from the second color space to a third color space and display, based on the segmentation data and the image data in the third color space, the image on the display device with an indication of the identified location of the features. The one or more features may include a type of tissue, an anatomical structure, or an external object introduced into a patient.

To identify the location of the feature in the image by analyzing the image data in the second color space, the computing device may be configured to generate a histogram of hue values of pixels in the image data based on the image data in the second color space and identify pixels that fall within a range of hues in the histogram that correspond to the features, wherein the segmentation data indicates the pixels falling with the range of hues in the histogram that correspond to the features.

To identify the location of the feature in the image by analyzing the image data in the second color space, the computing device may be configured to group pixels in the image data in the second color space into groups based on hue values of the pixels; determine a first group of pixels from among the groups of pixels; determine a second group of pixels from among the groups of pixels; select one of the first or second group of pixels based on a relative color difference between the first and second groups of pixels, wherein the segmentation data indicates the selected group of pixels.

To group pixels, the computing device may be configured to generate a histogram of hue values of pixels in the image data based on the image data in the second color space. To determine a first group of pixels, the computing device may be configured to determine a first set of pixels that fall within a first range of the hues in the histogram. To determine a second group of pixels, the computing device may be configured to determine a second set of pixels that fall within a second range of hues in the histogram. To select one of the first or second group of pixels, the computing device may be configured to select one of the first or second set of pixels based on a relative color difference between the first range of hues and the second range of hues.

The first color spaces may be one of RGB, YUV, YPrPb, or YcrCb. The second color space may be one of HSV, Lab, or HSY.

In another aspect, image data representing video captured by a video endoscopic device is accessed. The image data is encoded in a first color space. The accessed image data is converted from the first color space to a second color space, wherein the second color space is different than the first color space. A location of a landmark feature is identified in the video by analyzing the image data in the second color space. A position of the landmark feature is tracked over multiple frames of the image data. An anatomical model is generated based on the tracked landmark feature. A location of a target anatomical feature in the video is determined based on the anatomical model. The video is displayed with an indication of the location of the target feature.

Implementations may include one or more of the following features. For example, determining the location of the target anatomical feature may include determining the location of the target anatomical feature based on the anatomical model and known anatomical relationships between aspects of the model and the target anatomical feature. Generating an anatomical model based on the tracked landmark feature may include determining movement of the landmark feature based on changes in position of the landmark feature between the multiple frames and generating the anatomical model based on the movement of the landmark feature.

Identifying the location of the landmark feature in the image by analyzing the image data in the second color space may include generating a histogram of hue values of pixels in the image data based on the image data in the second color space and identifying pixels that fall within a range of hues in the histogram that correspond to the features, wherein the segmentation data indicates the pixels falling with the range of hues in the histogram that correspond to the features.

Identifying the location of the landmark feature in the image by analyzing the image data in the second color space may include grouping pixels in the image data in the second color space into groups based on hue values of the pixels; determining a first group of pixels from among the groups of pixels; determining a second group of pixels from among the groups of pixels; and selecting one of the first or second group of pixels based on a relative color difference between the first and second groups of pixels, wherein the segmentation data indicates the selected group of pixels.

Grouping pixels may include generating a histogram of hue values of pixels in the image data based on the image data in the second color space. Determining a first group of pixels may include determining a first set of pixels that fall within a first range of the hues in the histogram. Determining a second group of pixels may include determining a second set of pixels that fall within a second range of hues in the histogram. Selecting one of the first or second group of pixels may include selecting one of the first or second set of pixels based on a relative color difference between the first range of hues and the second range of hues.

The first color spaces may be one of RGB, YUV, YPrPb, or YcrCb. The second color space may be one of HSV, Lab, or HSY.

In another aspect, a system includes a video endoscopic device and a computing device. The video endoscopic device is configured to generate image data representing video captured by the video endoscopic device, wherein the image data is encoded in a first color space and transmit the image data to a computing device. The computing device is configured to receive the image data transmitted by the video endoscopic device; convert the received image data from the first color space to a second color space, wherein the second color space is different than the first color space; identify a location of a landmark feature in the video by analyzing the image data in the second color space; track a position of the landmark feature over multiple frames of the image data; generate an anatomical model based on the tracked landmark feature; determine a location of a target anatomical feature in the video data based on the anatomical model; displaying the video on a display device with an indication of the location of the target feature.

Implementations may include one or more of the following features. For example, to determine the location of the target anatomical feature, the computing device may be configured to determine the location of the target anatomical feature based on the anatomical model and known anatomical relationships between aspects of the model and the target anatomical feature. To generate an anatomical model based on the tracked landmark feature, the computing device may be configured to determine movement of the landmark feature based on changes in position of the landmark feature between the multiple frames and generating the anatomical model based on the movement of the landmark feature.

To identify the location of the feature in the image by analyzing the image data in the second color space, the computing device may be configured to generate a histogram of hue values of pixels in the image data based on the image data in the second color space; and identify pixels that fall within a range of hues in the histogram that correspond to the features, wherein the segmentation data indicates the pixels falling with the range of hues in the histogram that correspond to the features.

To identify the location of the feature in the image by analyzing the image data in the second color space, the computing device may be configured to group pixels in the image data in the second color space into groups based on hue values of the pixels; determine a first group of pixels from among the groups of pixels; determine a second group of pixels from among the groups of pixels; select one of the first or second group of pixels based on a relative color difference between the first and second groups of pixels, wherein the segmentation data indicates the selected group of pixels.

To group pixels, the computing device may be configured to generate a histogram of hue values of pixels in the image data based on the image data in the second color space. To determine a first group of pixels, the computing device may be configured to determine a first set of pixels that fall within a first range of the hues in the histogram. To determine a second group of pixels, the computing device may be configured to determine a second set of pixels that fall within a second range of hues in the histogram. To select one of the first or second group of pixels, the computing device may be configured to select one of the first or second set of pixels based on a relative color difference between the first range of hues and the second range of hues. The first color spaces may be one of RGB, YUV, YPrPb, or YcrCb. The second color space may be one of HSV, Lab, or HSY.

The details of one or more implementations are set forth in the accompanying drawings and the description below. Other features, objects, and advantages will be apparent from the description and drawings, and from the claims.

DESCRIPTION OF THE DRAWINGS

FIGS. 2A-2D illustrate an example of a video arthroscope that can be used with the system of FIG. 1.

DETAILED DESCRIPTION

The disclosures of International Patent Application No. PCT/US2013/027436 filed Feb. 22, 2013 entitled VIDEO ENDOSCOPIC SYSTEM, U.S. Provisional Application No. 61/708,157 filed Oct. 1, 2012 entitled ENDOSCOPE WITH LED ILLUMINATION, U.S. Provisional Application No. 61/668,743 filed Jul. 6, 2012 entitled ENDOSCOPE WITH LED ILLUMINATION, and U.S. Provisional Application No. 61/602,106 filed Feb. 23, 2012 entitled ENDOSCOPE WITH LED ILLUMINATION are hereby incorporated herein by reference in their entirety.

Figure 1:
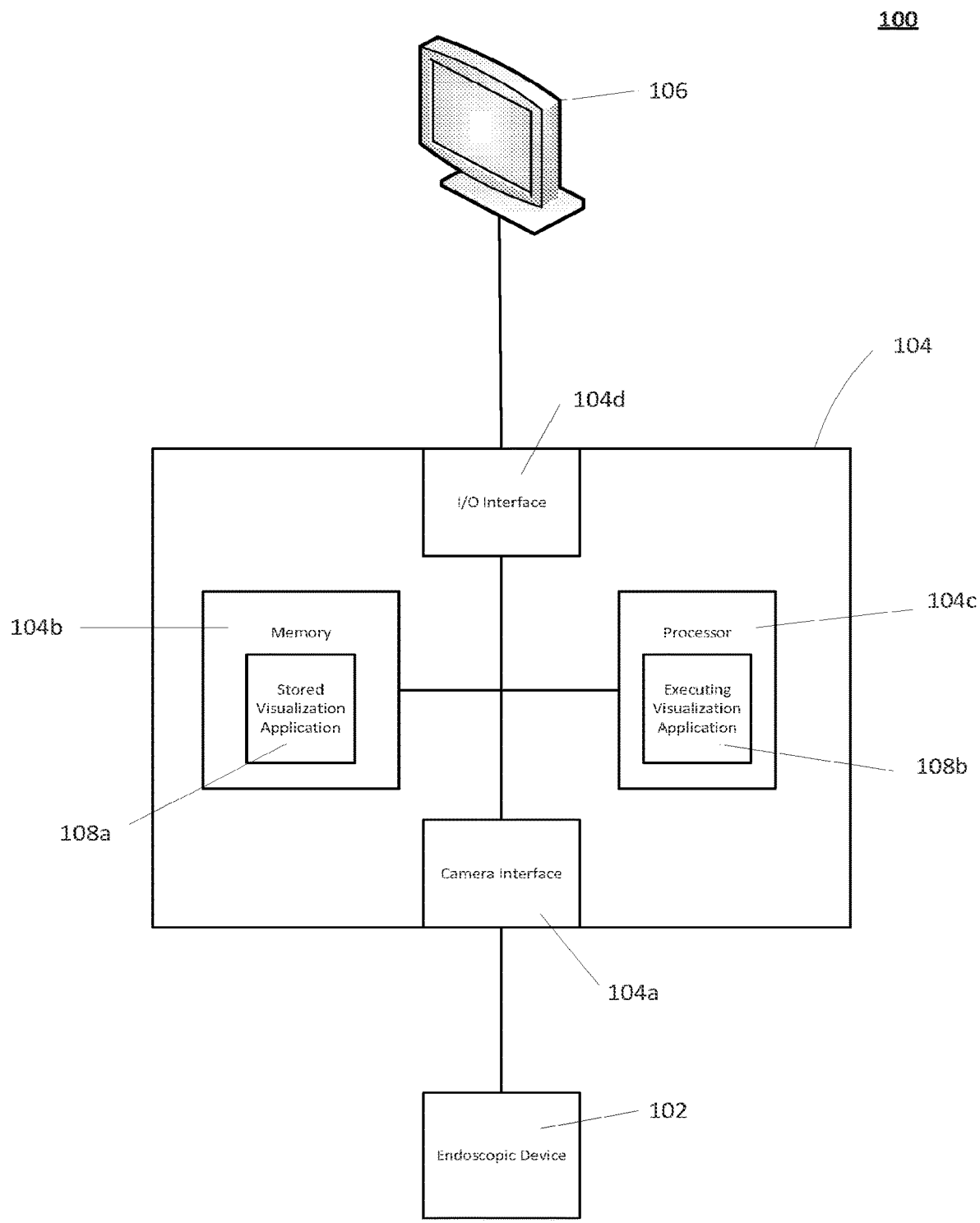
FIG. 1 is a block diagram illustrating an example of a medical system.

FIG. 1 is a block diagram illustrating an example of a medical system 100. The medical system 100 includes a video endoscopic device 102, such as a video arthroscope and image capture device, a computing device 104, and a display device 106. In general, the video endoscopic device 102 sends image data of internal anatomical structures to the computing device 104, which receives the image data 103 (e.g. via a video/frame capture device). The computing device 104 performs processing on the image data to segment target tissue or anatomical structures in the image data from other tissue or structures, and displays the corresponding images on the display device 106 in a manner that conveys the segmentation to the user, such as a surgeon.

In particular, the video endoscopic device 102 includes a rigid or flexible elongated insertion tube equipped with a set of optical fibers that extend from a proximal handle through the insertion tube to the distal viewing tip of the endoscope. The video endoscopic device is used to inspect regions within a patient's body (e.g., cavities, joints) during surgery (such as laparoscopic/arthroscopic surgery) by inserting the insertion tube through a small opening in the patient. One or more light sources are contained within the body of the video endoscopic device 102 and provide light to the optical fibers, which carry the light to the viewing tip. The light sources can be switched between providing broadband visible light and narrowband light suitable for causing autofluorescence of tissue or objects. In either case, an optical system of the video endoscopic device conveys the resulting image to a camera assembly that converts the image to a video signal that includes image data corresponding to the image.

The computing device 104 includes a camera interface 104a that receives the video signal from the video endoscopic device 102, and provides power to and bidirectional communication with the video endoscopic device 102. The computing device 104 may be any appropriate type of computing device such as a personal computer, workstation, portable computing device, console, laptop, network terminal, embedded device, or the like. The computing device 104 includes an interconnection mechanism such as a data bus or other circuitry that couples together the video input 104a to a memory system 104b, a processor 104c, and an input/output interface 114.

The memory system 104b is any appropriate type of computer readable device, which may include, for example, a floppy disk, a hard disk, Read Only Memory (ROM), or Random Access Memory (RAM). The memory system 104b stores a visualization application 108a. The stored visualization application 108a may include instructions that, when executed by the processor 104c, causes the processor to perform operations described below. During operation of the computing device 104, the processor 104c accesses the memory system 104b via the interconnect in order to execute the visualization application 108a. In other implementations, the processor 104c and memory system 104b may be replaced with a Field Programmable Gate Array (FPGA), which may be programmed to perform to execute the logic of the visualization application 108b.

The executing visualization application 108b causes the processor 104c to process the video signal in a manner that segments target tissue or anatomical structures in the image data in the video signal from other tissue or structures. For example, the processor 104c converts the image data from a first color space (for example, an RGB color space produced by the endoscopic device 102) to a second color space suitable for segmentation (for example, an HSV color space), and performs processing on the converted image data to perform segmentation. The processor 104c then converts the image data back into the first color space (or a different color space suitable for display) while maintaining the segmentation data, and uses the image data and segmentation data to display the video on the display device 106 in a manner that segments the target tissue or structure from other tissue or structures.

In another example, the processor 104c the processor 104c converts the image data from a first color space to a second color space suitable for segmentation, and performs processing on the converted image data to perform segmentation to identify landmark features. The processor 104c then tracks the landmark features, and uses the motion of the landmark features to generate an anatomical model. The processor 104c identifies target features based on the model, and displays video with an indication of the location of the target features.

FIGS. 2A-2D illustrate an example of a video arthroscope 200 that can be used with the system 100, for example, as the video endoscopic device 102. The video arthroscope 200 includes a rigid insertion tube 202 and a proximal body 204. The proximal body 204 includes an insertion assembly 206, a focus assembly 208, and a camera attachment assembly 210. The camera attachment assembly couples the video camera assembly 212 (otherwise referred to as the camera head) through, for example, a C-mount coupling 214. Using a C-mount coupling can allow the video arthroscope 200 and the camera head 212 to be detached and sterilized separately. In other implementations, the arthroscope 200 is coupled to the camera head 212 by an arthroscope coupler rather than a C-mount.

The insertion assembly 206 is coupled to the focus assembly 208 such that the insertion assembly 206 and focus assembly 208 can be rotated with respect to each other about the joint 216. Rotation of the insertion assembly 206 changes the field of view by changing the orientation of the distal end of the insertion tube 202.

The insertion assembly 206 includes an illumination post 218, which houses solid-state light sources 220 for generating light that is conveyed to and out of the distal end of the insertion tube 202 by illumination fiberoptic 222. The solid state light sources 220 include, for example, two LED light sources 220a and 220b.

The first LED light source 220a is a broadband LED light source that emits in visible broadband using, for example, phosphor conversion. For example, the broadband LED light source 220a may emit white light. The visible light is transmitted through, for example, a glass fiber bundle 222a with high transmission in the visible range. The fiber bundle 222a is, for example, butt coupled to the broadband LED light source 220a, and includes a high numerical aperture of about 0.86 NA, which may provide high coupling efficiency and illumination of the entire field of view.

The second LED light source is a narrowband LED light source that emits a narrow band of excitation light (for example, 395 nm) that can be used in auto-fluorescence imaging. The low wavelength light is transmitted through a plastic single or multiple fibers bundle 222b that is optimized for transmission at a lower wavelength.

The illumination can be switched by the user between visible and fluorescence excitation as needed. Having switchable light sources may allow the device to be used in surgery to distinguish tissue types. For example, in a patient with an anterior cruciate ligament (ACL) rupture, the device 200 can be switched to the narrow band autofluorescence (AF) mode so that the tissue of interest (remnant of the ACL at the insertion) can be identified for the purpose of determining where a drill tunnel should enter the bone for reconstruction. With a switchable light mode, the device 200 can be switched back and forth between visible light and autofluorescence mode to allow precise positioning of the drill guide/cannula at the desired insertion site. For instance, the surgeon may initially visualize the tissue of interest using autofluorescence, try to place the guide using visible light (because the drill guide end is easier to visualize in visible light), and then check the drill guide positioning relative to the tissue of interest using autofluorescence (and repeat until the guide is properly placed). Other types of tissue might also be identified using the autofluorescence mode, including damaged cartilage and/or meniscus tissue so that a subsequent procedure could be performed.

The focus assembly 208 includes a shank portion 223, a set of focusing optics 224, and a focus ring 226. The focusing ring 226 is configured to rotate relative to the shank portion 223 and the camera attachment assembly 210. Turning the focusing ring 226 adjusts the focusing optics 228 axially along a longitudinal axis of the device 200, which focuses the illuminated images.

During operation, the selected light source 220a or 220b provides illumination to a working area through the illumination fiberoptic 222. The illuminated images from the working area are conveyed to the camera assembly 212 through an optical path. The optical path extends from a distal end of the insertion tube 202, through an image fiberoptic 224 in the insertion tube 202, through a set of focusing optics 228 in focusing assembly 208 to video camera assembly 212, which includes a charged coupled device (CCD) assembly 230 to convert the images into image data. The CCD assembly may include, for example, a red CCD, a green CCD, and a blue CCD to generate RGB image data. In other cases, the CCD assembly may include, for example, a single sensor with a Bayer pattern configuration to deliver RGB data. The image data is conveyed in a video signal to the computing device 104.

The device 200 also includes a set of slip rings and wires to provide power from the camera head 212 to the light sources 220. In particular, the video arthroscope 200 includes a C-mount slip ring 232, a focus assembly slip ring 234, and an insertion assembly slip ring 236. The video arthroscope 200 also includes wires 238 that extend between the C-mount slip ring 232 and the focus assembly slip ring 234, and wires 240 that extend between the focus assembly slip ring 234 and the insertion assembly slip ring 240. A final set of wires extends from the insertion assembly slip ring 240 and the light sources 220. Electrical current is provided from the camera head 212 across the C-mount slip ring 232, through wires 234, across focus assembly slip ring 234, through wires 240, across insertion assembly slip ring 236, and finally through wires 242 to the light sources 220. The use of slip rings 232, 234, and 236 allow the camera head 212, focus ring 208, shank portion 223, and insertion assembly 206 to rotate with respect to one another as needed, while still having power conveyed from the camera head 212 to the light sources 220.

Figure 3:
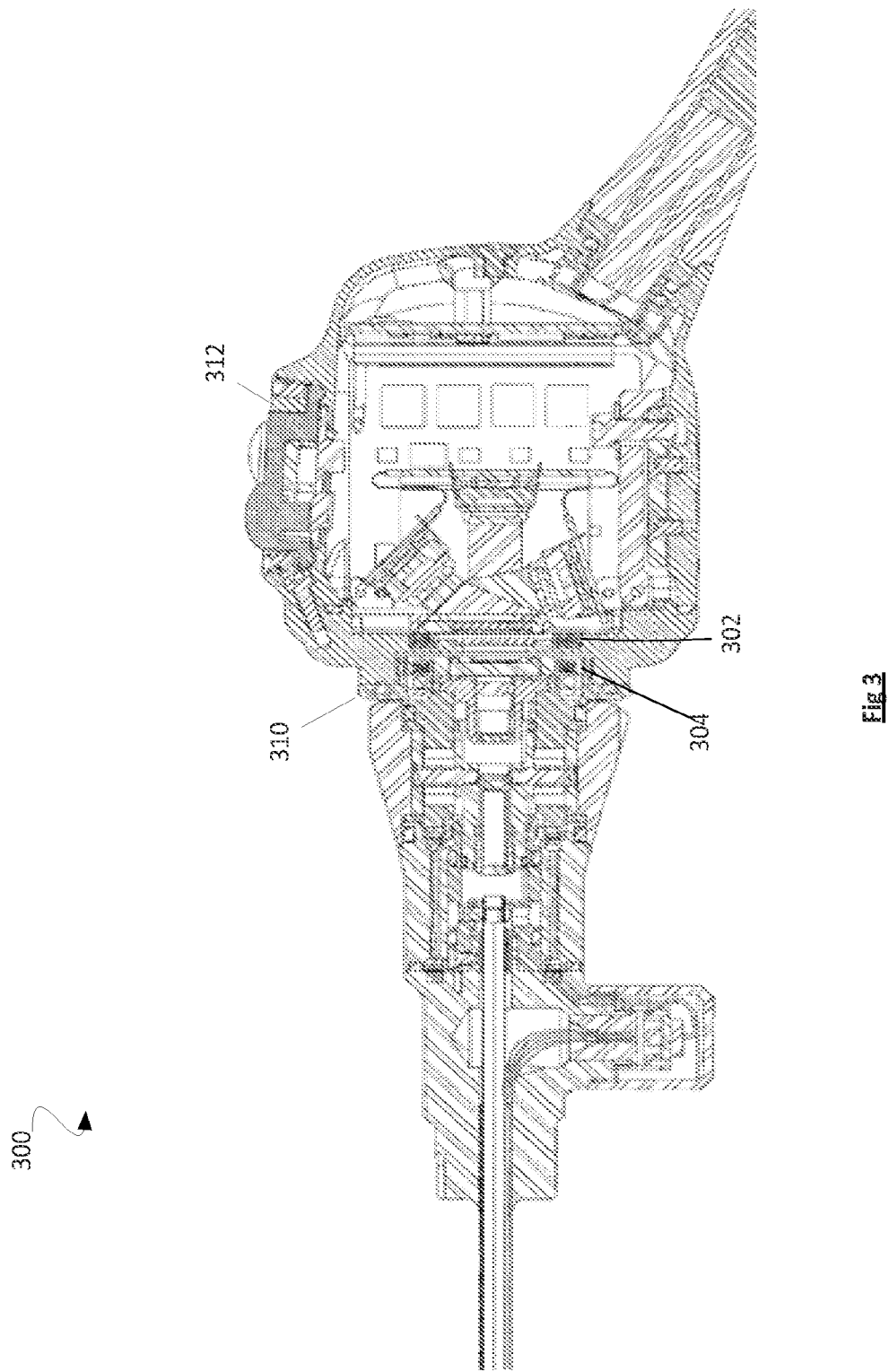
FIG. 3 illustrates an alternative example of a video arthroscope that can be used with the system of FIG. 1.

FIG. 3 illustrates an alternative example of a video arthroscope 300 that can be used with the system 100, for example, as the video endoscopic device 102. In this alternative, the electrical power is transmitted from the camera head to the video arthroscope through a wireless power transmission system. In particular, in the video arthroscope 300, the C-mount slip ring 232 is replaced with two coils 302 and 304. The first coil 302 (emitter) is placed in the camera head 312 and the second coil 304 (receiver) is placed in the video arthroscope in the camera attachment assembly 310. The first coil 302 transmits power to the second coil 304 using through inductive coupling using the near field. The power is then transmitted from the second (receiving) coil 304 through electrical wires and slip rings to the light sources in the same manner as described with respect to device 200.

In an alternative, the second coil 304 may be placed in the illumination post 218 or elsewhere in the insertion assembly 208. In this alternative, power is transmitted to the second coil 304 through far field coupling. Since the second coil 304 is located in the insertion assembly, the slip rings and the wires in the focus assembly 208 are not needed.

Figure 4:
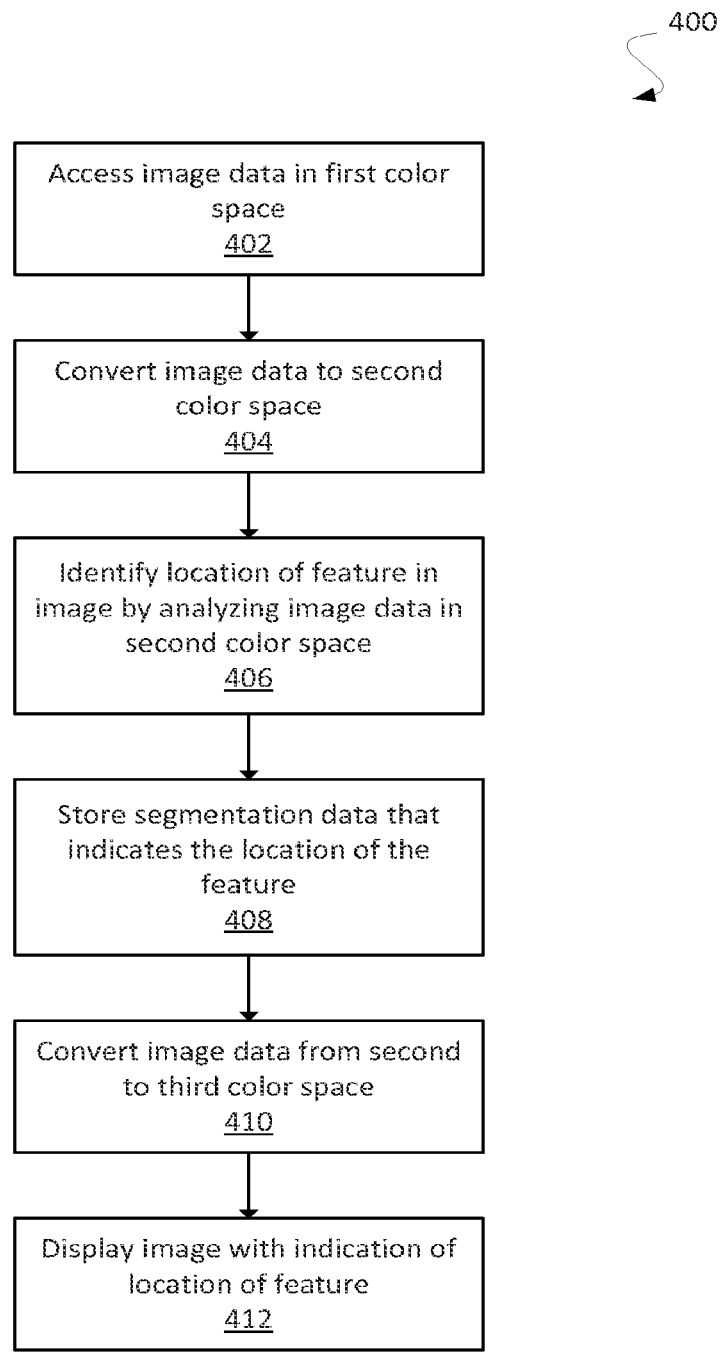
FIG. 4 shows an example of a process for segmenting features in image data, and displaying a corresponding image with the segmentation.

FIG. 4 shows an example of a process 400 for segmenting features in image data, and displaying a corresponding image with the segmentation. The process 400 is, for example, implemented by the processor 104c when executing the visualization application 108b, but other systems or configurations may perform the process 400. The process 400 enhances images captured by a video endoscopic device to better visualize areas of interest within the image field, be they anatomical aspects or external objects introduced into the field of view.

The processor 104c accesses image data representing an image captured by a video endoscopic device, such as a video arthroscope (402). The image data may correspond to an autofluorescence image captured using, for example, the narrowband light source 220b or a visible light image captured using, for example, the broadband light source 220a. The image may be of internal tissue or anatomical structures of a patient. The image data is encoded using a first color space that is appropriate for capture of the image (a capture color space). For example, the first color space is one of RGB, YUV, YPrPb, or YcrCb color spaces.

The processor 104c converts the accessed image data from the first color space to a second color space different from the first color space (404). The second color space is appropriate for segmentation of one or more areas of interest (a segmentation color space). The appropriateness of a color space as a segmentation color space is determined by its ability to discriminate individual colours, reduce color metamarism artifacts and allow for the most convenient implementation for support in the real-time processing unit. The second color space can be, for example, HSV, Lab, or HSY.

The processor 104c identifies a location of a feature in the image data by analysing the image data in the second color space (406). The feature may include tissue, an anatomical structure, or an external object introduced into the patient. To determine the feature, the processor 104c may, for example, perform color segmentation on the image data in the second color space to determine the features. As an example, after a fluorescent image is converted to the second color space (for example, HSV), the processor 104c may analyse the distribution of hues in the image, for instance, by generating a histogram of the hue values of the pixels in the image data in the second color space. Groups of pixels that correspond to different populations in the histogram (that is, different ranges of hues) may correspond to different tissues in the image. The processor 104c may identify the pixels that fall within the population (range of hues) in the histogram data that corresponds to the tissue of interest (or other features), and generate segmentation data that indicates the pixels falling within that population.

In another example, the processor 104c may use relative color differences to identify particular tissues, or to separate regions of an image corresponding to a tissue of interest from other regions of the image. For instance, in certain cases the hue of femoral ACL tissue is typically different from the hue of background portions of an image and other tissues. In autofluorescence images, for example, regions corresponding to an ACL often have a generally blue color, while background regions typically appear more purple. Thus background regions of an image are therefore typically red-shifted relative to regions showing ACL tissue. The processor 104c can use this information to distinguish ACL tissue from the background.

For instance, pixels in an autofluorescence knee image may be grouped according to hue values of the pixels (for example, using a histogram or other technique). A first group and a second group of pixels is then identified from among the groupings. For instance, when a histogram is used, the processor 104c can determine first and second sets of pixels that fall within first and second ranges of hues, respectively, in the histogram. The first and second groups may be identified by, for example, first eliminating extraneous information that does not meet a minimum saturation value as well as minimum intensity value, then correlating the remaining populations to Gaussian distributions to identify distinct populations within the histogram, or alternatively employing a multistage detection algorithm including low pass filtering and outlier elimination then detecting populations by thresholding of first and second derivatives with the goal of identifying distinct populations in the processed hue histogram distribution. Out of the first and second groups, the processor 104c selects the group with bluer pixels (relative to the other group) as corresponding to ACL tissue and generates segmentation data that indicates these pixels. When a histogram is used, the processor 104c can select the set of pixels that fall within the range of hues that is bluer.

In a similar manner, analysis of the distribution of pixels according to hue may indicate additional or different regions in an image. In some implementations, a group of pixels that includes the largest number of pixels may be designated as background, since the background is typically the largest area of an image.

In some situations, the interoperability of different optics, camera sensors, and processing systems is enhanced by analysing the distribution of hues in an image. Under the same lighting conditions, different devices and device configurations may produce a range of different absolute hues. Nevertheless, analysis of the distribution of hues in an image (e.g., differences in hue among different regions of an image) can permit reliable precision despite these variations.

The processor 104c stores the segmentation data that indicates the location of features in the image data (408) and converts the image data from the second color space to a third color space (410). The third color space is appropriate for display on a display device and may, for example, be one of RGB, YUV, YPrPb, or YcrCb.

Based on the segmentation data and the image data in the third color space, the processor 104c displays the image with an indication of the identified location of the features (412). The location of the features can be identified, for example, by a binary mask that is used to overlay a pseudo colour onto a grayscale representation of the original image before processing. As another example, the segmentation data can be used to generate a mask that is directly mapped to one of the standard RGB channels and excluded from the remaining channels such that the segmentation only appears in one of those display channels. Also, for instance, the segmentation data can be processed further to create an outline region to be alpha blended onto the original image as an overlay.

While described above with respect to system 100, the process 400 can be performed independent of the particular vehicle for capturing the auto fluorescent, fluorescent, or visible energy image. In some implementations, tissue boundaries (e.g., edges) or other regions of interest are detected and overlayed with live video output from a video arthroscope.

In some cases, process 400 can be performed to aid in visualizing features of interest without pre-defined calibration. Other processes may require a priori knowledge of the system's signal response through optics, camera sensor, any pre-existing processing pipeline under excitation illumination and may need to support a calibration to correct for variations in each individual system's optical and electronic response in order to adequately separate the signal response of the target tissue or object from that of the background system response. Process 400 may not need such calibration under appropriate circumstances.

Figure 5A:
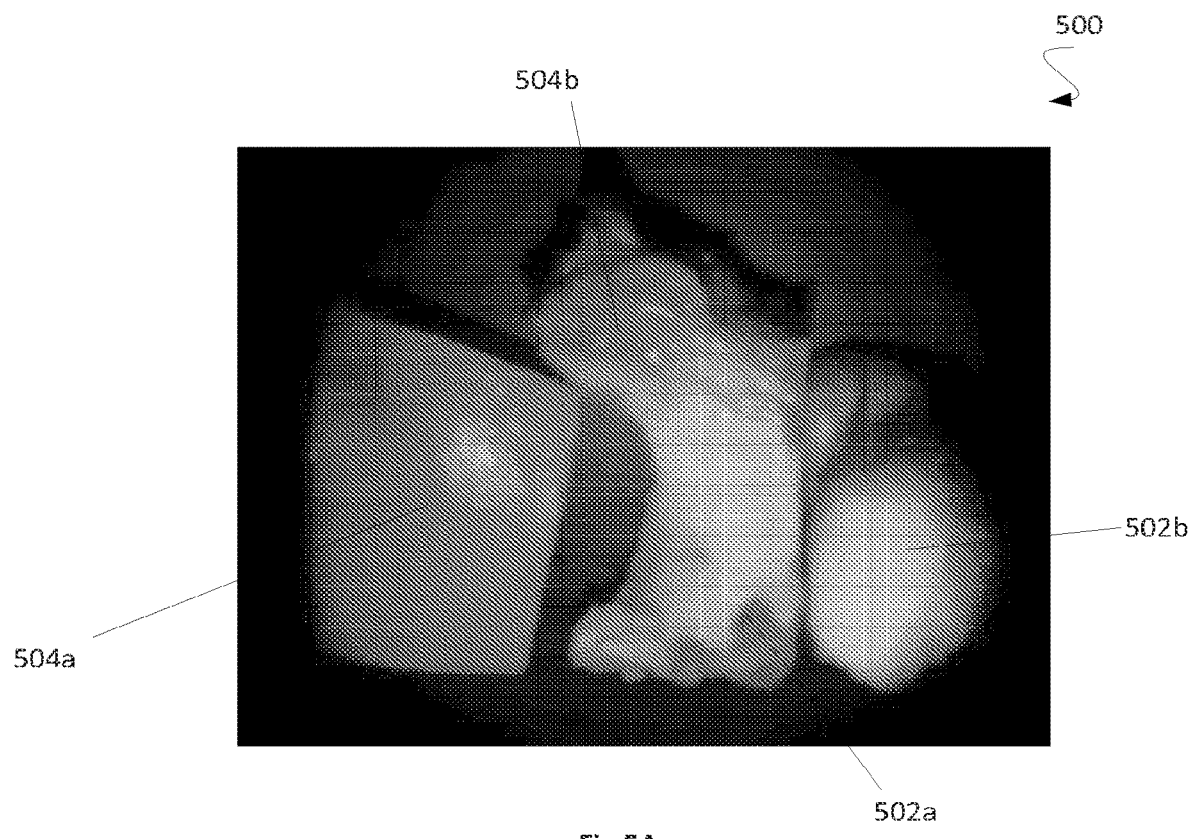
FIG. 5A is an illustration showing an example of an autofluorescent image captured in RGB space.

FIG. 5A is an illustration showing an example of an autofluorescent image 500 captured in RGB space. The image 500 may be captured, for example, using the narrowband light source 220b. The image is of tissue samples from a human knee, which includes a femoral ACL footprint area 502a and 52b and cartilage 504a and 504b from the femoral condyle. Both of these structures have collagen, but the ACL has different type of collagen, which results in the femoral footprint 502a and 502b fluorescing in a light blue color, while the cartilage 504a and 504b fluoresces purple. The ACL footprint in this example is the anatomical feature of interest.

Figure 5B:
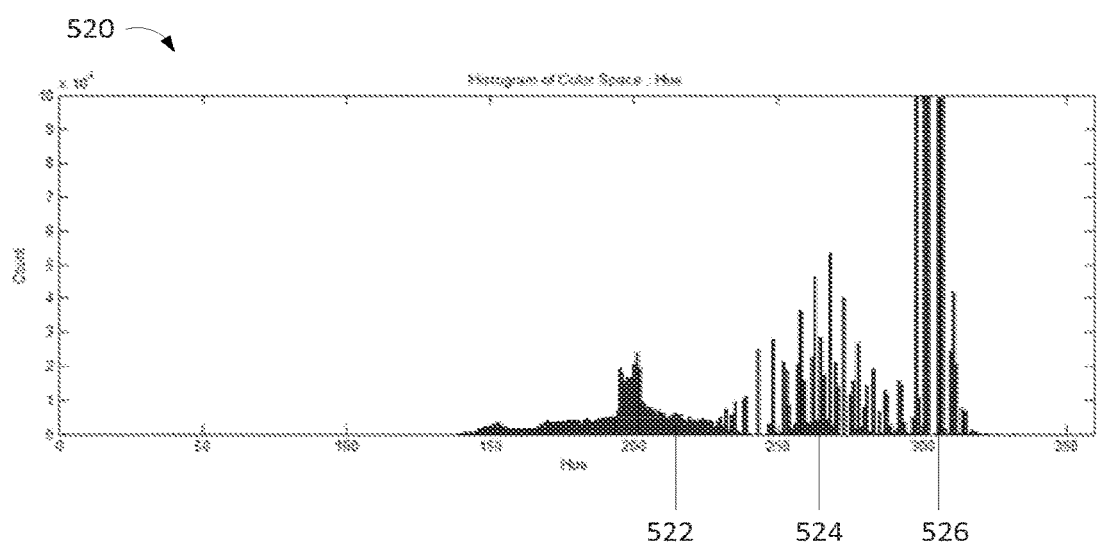
FIG. 5B shows an example of a histogram generated based on the image of FIG. 5A after the image is converted to an alternate color space.

FIG. 5B shows an example of a histogram 520 generated based on the image 500 after the image 500 has been converted to an alternate color space, such as HSV. The histogram has three major groupings of pixels. The first group 522 is centered around 200 degrees. The second group 524 is centered around 275 degrees. The third group 526 is centered around 315 degrees. The third group 526 includes the highest count of pixels and may therefore be designated as the background (in some implementations, these pixels may have been filtered out prior to forming the histogram). In this case, the first and second groups 522 and 524 correspond to the two types of tissue. Since ACL tissue is more blue relative to the cartilage of the femoral condyle, the bluer group of pixels (the first group 522) is selected as corresponding to the ACL tissue.

Figure 5C:
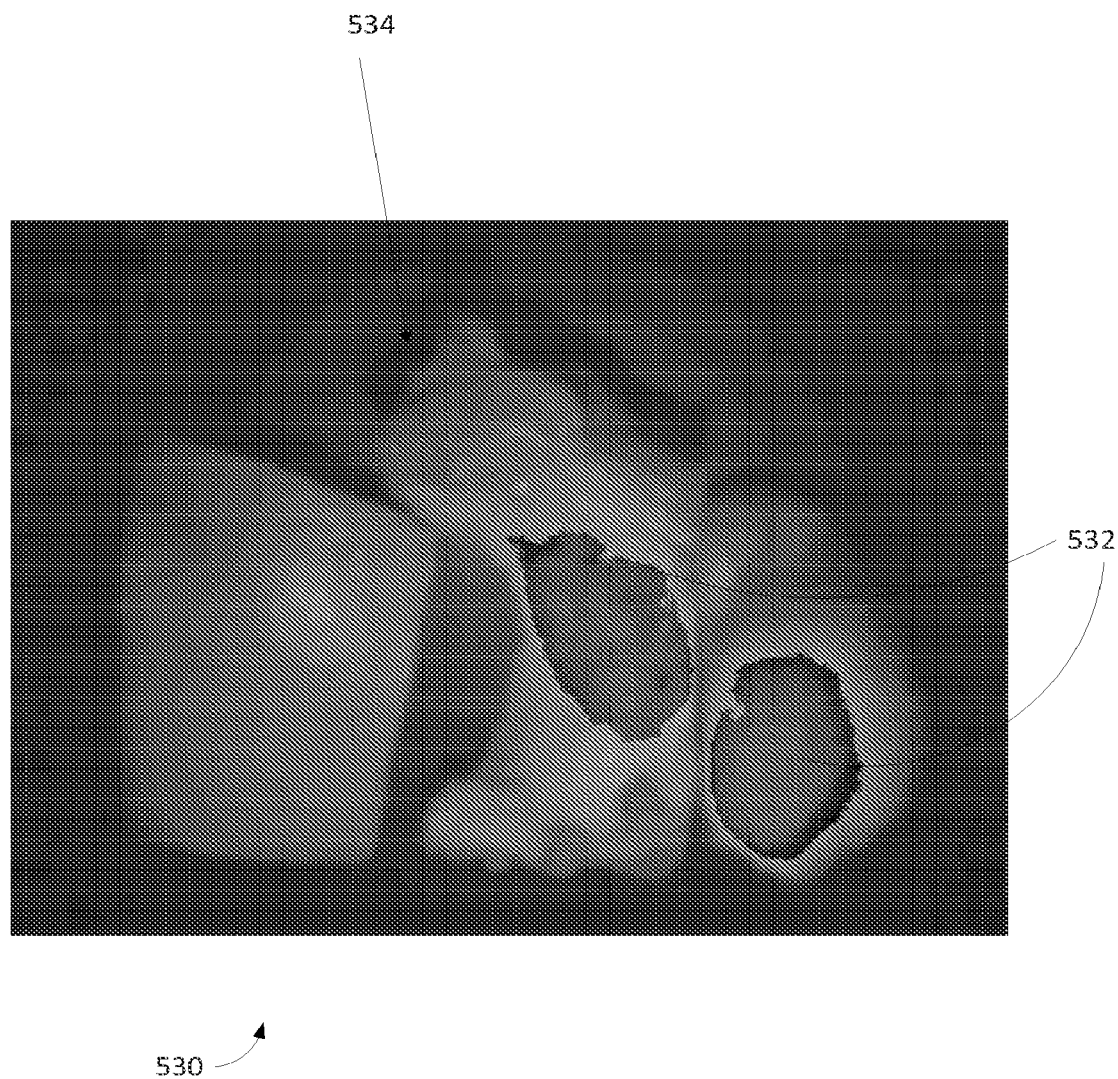
FIG. 5C is an illustration showing an example of an image with a segmentation mask derived from the populations of FIG. 5B.

FIG. 5C is an illustration showing an example of an image 530 with a segmentation mask 532 derived from the populations of histogram 520. The segmentation mask indicates the location of the ACL footprint (the anatomical feature of interest). In this case, the original image is sent on the green channel of a display and the segmentation mask is sent on the red channel of the display. This results in a red segmentation mask 532 being shown over the features of interest (the ACL footprint), while the rest of the anatomical features are shown in green.

Figure 6:
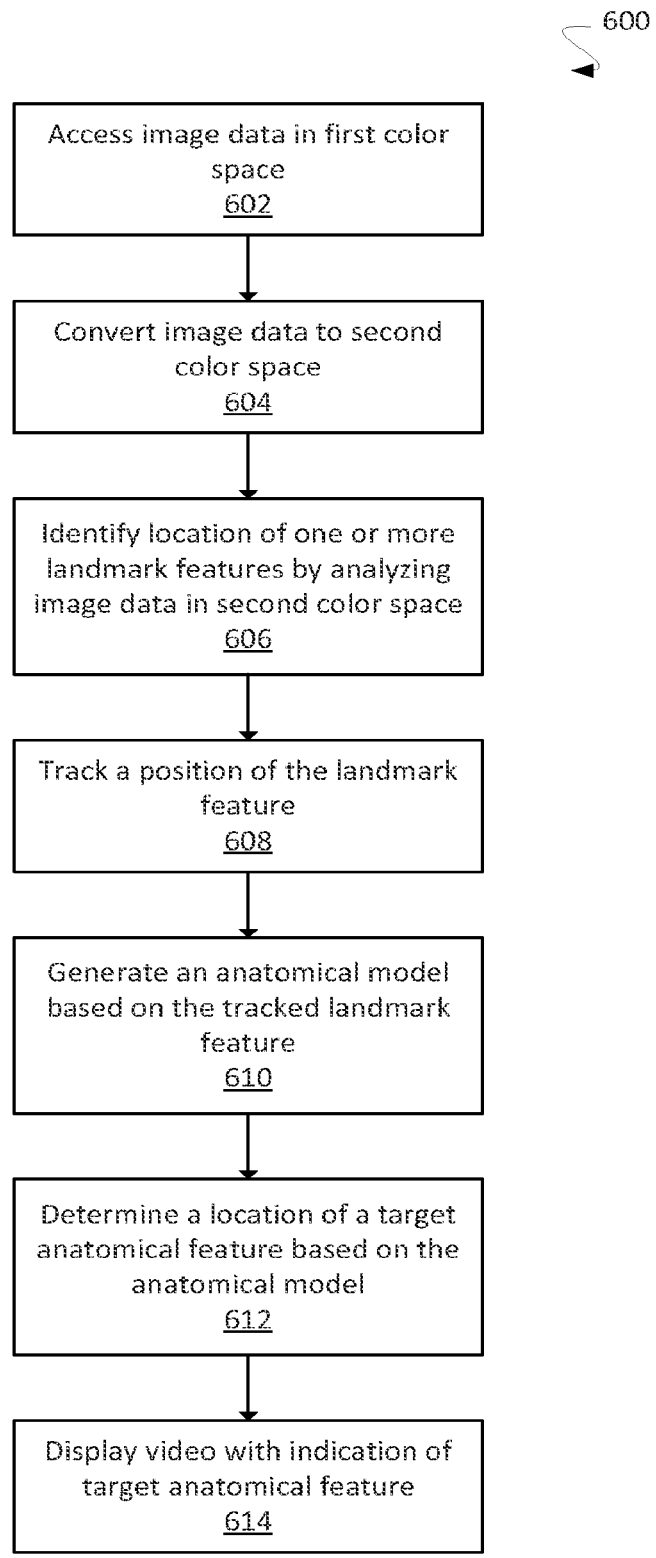
FIG. 6 shows an example of a process for identifying features in image data and using those features in an anatomical model.

FIG. 6 shows an example of a process 600 for identifying features in image data and using those features in an anatomical model. The process 600 is, for example, implemented by the processor 104c when executing the visualization application 108b, but other systems or configurations may perform the process 400.

In general, the process 600 uses color space conversion for segmentation, such as described with respect to process 400, to identify landmark features in imaged anatomy and use those landmark features, potentially with other landmark features, to build a feature based model composed of known anatomical points. This model can then be used to identify target anatomical features or area in the field of view and display target features or areas in a manner that distinguishes them from other areas. In some cases, autofluorescence imaging data can enhance the performance of a feature-based model that represents imaged tissue.

The processor 104c accesses image data encoded in a first color space, for example, in the form of a live video from an arthroscope (602). The image data may correspond to an autofluorescence image captured using, for example, the narrowband light source 220b or a visible light image captured using, for example, the broadband light source 220a. The image may be of internal tissue or anatomical structures of a patient. The image data is encoded using a first color space that is appropriate for capture of the image (a display color space). For example, the first color space is one of RGB, YUV, YPrPb, or YcrCb color spaces.

The processor 104c converts the accessed image data from the first color space to a second color space different from the first color space (604). The second color space is appropriate for segmentation of one or more areas of interest (a segmentation color space), as described above with respect to action 404.

The processor 104c identifies locations of one or more landmark features in the image data by analysing the image data in the second color space (606). The processor 104c does so, for example, using any of the techniques described above with respect to action 406. The processor 104c can also identify the location of additional landmark features, such as points or edges, using the image data in the first or second color spaces.

The processor tracks the position of the landmark features across multiple frames of video (608). The multiple frames of video may capture the landmark features at different positions with respect to the subject (e.g., video is captured from multiple perspectives). Based on the changes in position of the tracked features, the processor uses, for example, motion estimation techniques to estimate the manner in which the features have moved. For example, the processor determines motion vectors that describe the manner in which the tracked features moved.

The processor generates a three-dimensional (3D) feature-based anatomical model based on the movement of the tracked features (610). Once the 3D model is generated, the processor determines the location of a target anatomical feature (612). For example, when the model represents a portion of a femur, an ACL or PCL location may be determined based on aspects of the model. The processor may estimate the location of an anatomical feature by taking into account known anatomical relationships, such as ratios, proportions, and other characteristics of anatomical features. For example, the curvature of a femoral condyle may be determined based on the 3D model. Using this curvature value, the position of an ACL, PCL, or other feature may be determined relative to the 3D model, based on a known ratio describing size and placement of knee features.

The processor then displays the images corresponding to the image data with an indication of the location of the target anatomical feature (614). For example, the location of the anatomical feature of interest is indicated on the live video feed from the arthroscope as an overlay. The processor continues to track the position of the tracked features. As the view of the subject changes, the processor updates the video display to show changes in the position of the anatomical feature of interest. Additional feature localization and visualization techniques may be used, including those described in U.S. patent application Ser. No. 12/967,435, filed Dec. 14, 2010 (and published as U.S. Patent App. Pub. No. 2011/0141140), which is incorporated herein by reference in its entirety.

A number of implementations have been described. Nevertheless, it will be understood that various modifications may be made. For example, while examples of image processing and modelling techniques have been described for use with video arthroscopes, the same techniques may be used with other devices and forms of image capture.

Figure 2C:
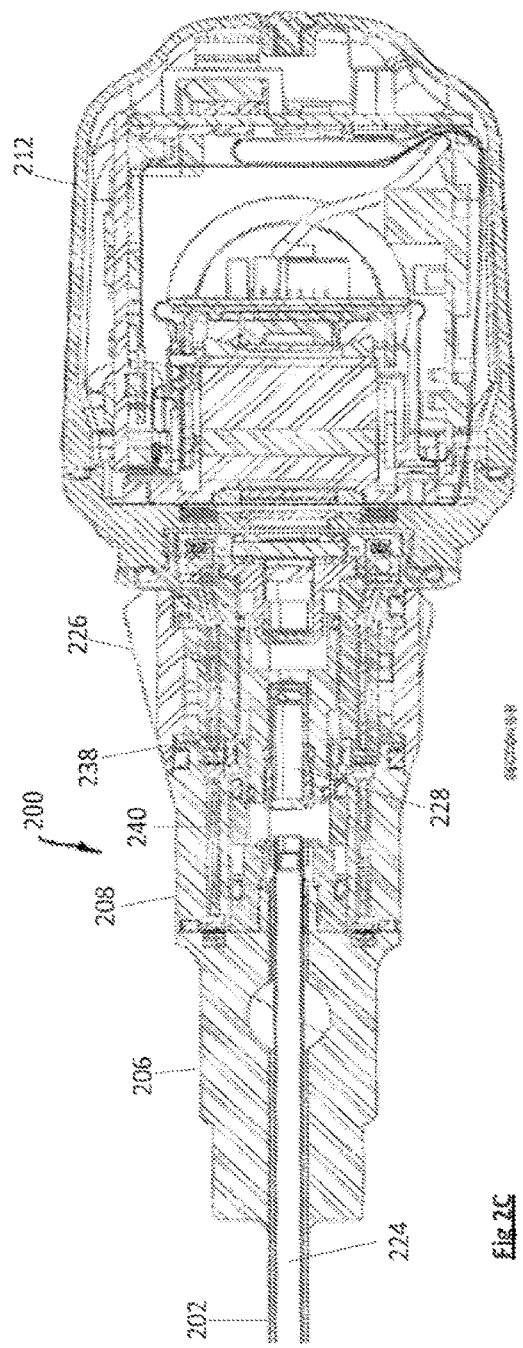
Figure 2D:
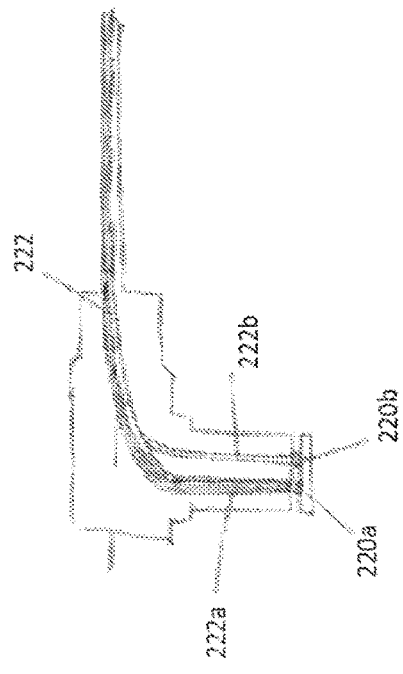

Further, autofluorescence imaging can be performed using any appropriate device or combination of devices, and is not limited to the particular devices described. For instance, FIG. 2D shows a configuration where the visible light source and the narrow band light source for excitation are formed from separate LEDs that are both mounted in the sidearm. It is possible that one light source, made of a multitude of chips emitting in different colours, is located in the side arm or in any other location in the endoscope and can be switched between visible light and light suitable for autofluorescence. Such an LED light source can be referred to as a tunable White LEDs and can be used to switch as needed between visible light or fluorescence excitation light. If a LED (or other solid state technology) becomes available that can be switched or changed from broad band to narrow band light emission, it could be used instead of the two LED's shown in FIG. 2D.

Illumination for both visible or fluorescence excitation may be delivered in a manner other than an illumination channel of an endoscope. For example, florescence excitation can be delivered through a probe separate from the video arthroscope. In this case, the visible light source may be mounted in the video arthroscope, with the LED source for fluorescence being placed in a separate probe or instrument. The LED source for fluorescence can be disposed at a distal or proximal end of the individual probe. If the LED source for fluorescence is placed at the proximal end, the excitation energy may be delivered distally through a fiber. The LED for fluorescence and/or fiber delivering the excitation energy for fluorescence can be embedded in other types of instruments used in arthroscopic procedures, such as a drill guide, hand instrument, or a reusable or disposable cannula that fits around the drill guide, endoscope or separate probe. In addition, the illumination can be generated on an independent self-powered device and delivered to the delivery device via a flexible light guide coupled by a post on the delivery device. In this last embodiment, the excitation energy can be generated by a monochromatic laser, LED or a filtered white light source in the standalone device.

Accordingly, other implementations are within the scope of the following claims.

What is claimed is:

1. A video endoscopic device, comprising:
a video camera assembly extending along an axis and including a camera interface and a first coil; and
a proximal body extending from the video camera assembly along the axis and including:
an illumination post extending transverse to the axis having one or more light sources configured to emit a visible light having a visible wavelength within a visible light range and an excitation light having an excitation wavelength shorter than the visible wavelength operable to excite tissue of interest using autofluorescence, and
a second coil electrically coupled to the one or more light sources,
wherein the video camera assembly is coupleable to the proximal body,
wherein the camera interface is operative to provide power for transmission to the first coil,
wherein the first coil is operative to transmit the power, through inductive coupling, to the second coil, and
wherein the visible light is broadband light and the excitation light is narrowband light.

2. The video endoscopic device of claim 1 wherein the first coil is further operative to transmit the power, through the inductive coupling, to the second coil for transmission to the one or more light sources.

3. The video endoscope device of claim 1 wherein the first coil is operative to transmit the power to the second coil through near-field coupling.

4. The video endoscope device of claim 1 wherein the first coil is operative to transmit the power to the second coil through far-field coupling.

5. The video endoscopic device of claim 1 wherein the video camera assembly and the proximal body are free to rotate around the axis, thereby providing optical focusing and direction of view changes during use of the video endoscopic device.

6. The video endoscopic device of claim 1 wherein the one or more light sources comprises a tunable light emitting diode configured to selectively emit the visible light and the excitation light.

7. The video endoscopic device of claim 1 wherein the one or more light sources comprises a first light source configured to emit the visible light and a second light source configured to emit the excitation light.

8. The video endoscopic device of claim 7 further including:
a first fiber bundle abutting the first light source and configured for light transmission in the visible light range from the first light source through the proximal body; and
a second fiber bundle abutting the second light source and configured for light transmission of light having a shorter wavelength than the visible light range from the second light source through the proximal body.

9. The video endoscopic device of claim 1 wherein the video camera assembly includes a charge coupled device with a Bayer pattern configuration to deliver red, green, and blue image data.

10. The video endoscopic device of claim 1 wherein the second coil is disposed in the illumination post.

11. The video endoscopic device of claim 1 wherein the visible light is a white light and the excitation light has a wavelength of 395 nanometers.

* * * * *